(12) United States Patent
Meyer

(10) Patent No.: US 8,512,558 B2
(45) Date of Patent: Aug. 20, 2013

(54) MAGNETIC SEPARATION SYSTEM COMPRISING FLEXIBLE MAGNETIC PINS

(75) Inventor: Thomas Meyer, Cham (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 573 days.

(21) Appl. No.: 12/709,085

(22) Filed: Feb. 19, 2010

(65) Prior Publication Data

US 2011/0203997 A1    Aug. 25, 2011

(51) Int. Cl.
*B01D 35/06* (2006.01)
*B01L 3/00* (2006.01)

(52) U.S. Cl.
USPC ........... 210/222; 210/695; 422/553; 422/509; 422/513; 422/503; 436/177

(58) Field of Classification Search
USPC ................. 210/222, 223, 695; 422/500, 501, 422/502, 503, 509, 513, 521, 527, 534, 551–554; 436/177
See application file for complete search history.

(56) References Cited

U.S. PATENT DOCUMENTS

| | | | | |
|---|---|---|---|---|
| 4,272,510 A | * | 6/1981 | Smith et al. | 427/598 |
| 4,345,843 A | * | 8/1982 | Berglund et al. | 366/219 |
| 4,571,768 A | * | 2/1986 | Kawashima | 15/167.1 |
| 4,988,618 A | | 1/1991 | Li et al. | |
| 5,558,839 A | * | 9/1996 | Matte et al. | 422/552 |
| 5,567,326 A | * | 10/1996 | Ekenberg et al. | 210/695 |
| 5,779,907 A | | 7/1998 | Yu | |
| 5,802,656 A | * | 9/1998 | Dawson et al. | 15/110 |
| 6,645,431 B2 | * | 11/2003 | Astle | 422/527 |
| 6,672,458 B2 | * | 1/2004 | Hansen et al. | 209/224 |
| 6,884,357 B2 | * | 4/2005 | Siddiqi | 210/695 |
| 7,776,221 B2 | * | 8/2010 | Brassard | 210/695 |
| 8,071,395 B2 | * | 12/2011 | Davis et al. | 436/524 |
| 8,317,389 B2 | * | 11/2012 | Jagle | 366/208 |
| 2003/0038071 A1 | * | 2/2003 | Hansen et al. | 210/222 |

FOREIGN PATENT DOCUMENTS

| | | |
|---|---|---|
| EP | 1681570 A2 | 7/2006 |
| EP | 1681570 B1 | 11/2008 |
| GB | 2300258 A | 10/1996 |
| WO | 2005044460 A2 | 5/2005 |

* cited by examiner

*Primary Examiner* — David C Mellon
(74) *Attorney, Agent, or Firm* — Olga Kay

(57) ABSTRACT

A magnetic separation plate for use in methods employing magnetic particles, said magnetic separation plate comprising a support plate and magnetic pins in a predetermined geometrical arrangement, said magnetic pins having a fastening portion, an intermediate portion and a separation portion and being fastened to said support plate at their fastening portion, wherein said magnetic pins are individually displaceable at their separation portion. The invention further provides a method for the separation of magnetic particles using the separation plate.

8 Claims, 3 Drawing Sheets

MAGNETIC SEPARATION SYSTEM COMPRISING FLEXIBLE MAGNETIC PINS

FIELD OF THE INVENTION

The present invention belongs to the field of analytics, particularly the separation and/or isolation of biological materials such as nucleic acids or proteins in or from complex mixtures. Within that field, the present invention relates to magnetic separation.

BACKGROUND OF THE INVENTION

The separation of magnetic or magnetizable components such as magnetic particles on the to basis of magnetic forces has been of considerable significance particularly in the field of analytics.

Magnetic particles can, for instance, be used as a binding support for biological materials such as proteins or nucleic acids. In an exemplary typical analytical setting, the magnetic particles are contacted with a liquid sample containing an analyte in a multiwell plate, under conditions that facilitate binding of the analyte to the magnetic particles. The latter can then be subsequently separated from the liquid by means of magnetic forces generated by magnetic pins. U.S. Pat. No. 5,779,907 discloses a device in which such magnetic pins are attached to a base plate, wherein the multiwell plate containing sample and magnetic particles is exposed to a magnetic field generated by the magnetic pins upon physical combination of the pin-bearing base plate with said multiwell plate. In order to invoke a significant magnetic field within the sample fluids, the magnetic pins are moved into close vicinity to the wells by means of being introduced into preadapted recesses in locations of the multiwell plate not containing any samples.

However, the coupling of the above-mentioned plates to each other gives rise to the following problem: When the magnetic pins are being placed into the preadapted recesses within the multiwell plate, tolerances with respect to size and position of the pins and recesses frequently lead to jamming of the system or breakage of the pins as the latter cannot be easily inserted into and/or removed from the recesses.

In the prior art, this problem has been tackled in various manners:

The diameter of the recesses within the multiwell plate has been increased in relation to the diameter of the magnetic pins The above-mentioned tolerances have been controlled more strictly Deformability of the multiwell plate has been enhanced.

The present invention provides an alternative solution displaying several advantages.

DESCRIPTION OF THE INVENTION

The present invention provides a magnetic separation plate including flexible or flexibly fastened magnetic or magnetizable pins. New methods and uses comprising this plate are further provided. According to the invention, the plate can also be part of magnetic separation system further comprising a multiwell plate. Also, one aspect of the invention is an analytical system for the processing and/or analysis of a sample, wherein the aforementioned magnetic separation system is a part of the analytical system. In a first aspect, the invention is related to the following:

A magnetic separation plate for use in methods employing magnetic particles, said magnetic separation plate comprising a support plate and magnetic pins in a predetermined geometrical arrangement, said magnetic pins having a fastening portion, an intermediate portion and a separation portion and being fastened to said support plate at their fastening portion, wherein said magnetic pins are individually displaceable at their separation portion.

The present invention features an advantageous possibility to establish reliable and automatable methods for magnetic separation, as the latter require the process of coupling a multiwell plate and the magnetic separation plate to be reversible.

Especially upon reduction of the size of a magnetic separation device or system, or the reduction of well diameter due to the presence of a higher number of wells in medium or high throughput systems, measures like widening the multiwell recesses or strictly controlling the production-caused tolerances in the recesses' diameter become considerably more difficult to achieve and thus less appropriate to remedy the technical problem set out supra.

The solution according to the present invention, on the other hand, is particularly useful in the context of striving to minimize the dimensions of separation devices in favor of enhancing sample throughput. Inherent flexibility and/or flexible fastening of the magnetic pins are not negatively affected by reducing the device's or system's size and therefore the distances between the distinct elements.

Multiwell plates with recesses of comparatively small diameters with relatively high tolerances may be used in the system according to the invention, which simplifies the production of such plates and reduces the respective costs.

Furthermore, mechanical stress exerted upon the magnetic pins due to the technical problem described above is compensated for according to the present invention, thus increasing their stability and duration. Moreover, the flexibility and/or flexible fastening of the pins generally reduce the force that is required to insert them into the recesses of the multiwell plate.

In some of the alternative solutions to the technical problem mentioned above, the homogeneity and/or overall intensity of the magnetic field acting on the magnetic particles can be affected in a negative manner. For example, recesses that are significantly wider than the magnetic pins to be inserted inevitably lead to an increase of the distance between pin and sample, thus decreasing the magnetic force the particles are exposed to. Further, the tolerances in the positions of the wells may cause an inhomogeneous magnetic field, since the distances between distinct pins and recesses may vary compared to each other. The present invention enables the artisan to apply a homogeneous field throughout the wells of the multiwell plate, said field being close to its maximum possible intensity, since small recesses can be used with the magnetic pins adapting the position of their separation portion to possible deviations of the geometrical arrangement of the recesses.

A "magnetic separation plate" is a device useful for the separation of magnetic particles. It comprises a "support plate" and "magnetic pins", wherein the "support plate" is typically an essentially flat device for bearing and holding the "magnetic pins" in a defined position which is usually perpendicular to the support plate. Said plate can be made of one or more parts and different materials such as metal or plastic. In a preferred embodiment, the plate is made of metal. Preferably, the support plate comprises an upper and a lower plate fastened to each other.

In preferred embodiments, the "magnetic pins" are essentially rod-shaped magnetic or magnetizable structures. The length of the magnetic pins is preferably 2-100 mm, more preferably 15-50 mm. Their diameter is preferably 1-20 mm, more preferably 2-6 mm. The pins comprise a "fastening portion", an "intermediate portion" and a "separation portion". However, in the context of the invention, this tripartite structure is not necessarily to be understood as an assembly of morphologically distinct and visually clearly separable or distinguishable structures. It is rather preferred that the different portions are integrally linked to each other in a manner such that there is no visible transition between them.

The "fastening portion" is the portion at the end of the pin at which it is fixed to the support plate. If the "support plate" comprises an upper and a lower plate fastened to each other, the "fastening portion" is preferably embedded in between the upper and the lower plate.

The "separation portion" is located at the end of the pin opposite to the fastening portion and separates the magnetic particles within the wells of a multiwell plate. A part or all of said "separation portion" is inserted reversibly into recesses within a multiwell plate. Said "separation portion" is morphologically preadapted to fit into said recesses. Therefore, in a preferred embodiment, the "separation portion" has a rounded-off tip at the end of the pin opposite of the fastening portion. The "separation portion" can be made of flexible and/or rigid material. Preferably, it is made of the same material as the remainder of the magnetic pin.

The "intermediate portion" designates an integral portion of the magnetic pin located between and physically coupling the "fastening portion" and the "separation portion". The "intermediate portion" is functionally distinct from the "fastening portion" and the "separation portion". The "intermediate portion" can further be magnetic or magnetizable even though it does not directly contribute to the magnetic separation, and it can further be made of flexible and/or rigid material. It has preferably the same diameter and is preferably made of the same material as the "separation portion". The length of the intermediate portion is variable and can be very short.

In the absence of external forces acting on the magnetic pins, the angle between the pins and the support plate is essentially a right angle. In a preferred embodiment of the invention, the angle is between 80 and 100°, more preferably between 85° and 95°, most preferably 90°.

A "predetermined geometrical arrangement" in the context of the invention means a defined spatial and directional relation between elements of a group of physical objects such as magnetic pins.

"Individually displaceable" means that elements of a group of physical objects such as magnetic pins can be displaced independently from each other, i.e. moving one element does not affect other elements of this group. In the context of the invention, the magnetic pins are preferably laterally displaceable up to 5 mm from their default position at their separation portion, more preferably up to 1 mm.

In a preferred embodiment, the magnetic pins return to their default position when external forces (as e.g. exerted by a microwell plate) are removed. Said return to the default position is caused by reset forces exerted by their specific structure and/or fastening to the support plate.

At their fastening portion, the magnetic pins can be laterally displaceable up to 2 mm distance from their default position, more preferably up to 0.2 mm.

A further aspect of the invention is the magnetic separation plate described above, wherein the magnetic pins are flexibly fastened to said support plate.

"Flexibly fastened" means that the pins are not attached to the support plate in a rigid manner, but can be tilted with respect to the support plate such that the pins can be laterally displaced at their separation portion.

In order to achieve this, there are different advantageous possibilities.

In a preferred embodiment, the magnetic pins are fastened to the support plate via a holder containing one or more flexible elements.

A "holder" in the context of the invention is a mount for the magnetic pins and can for example be a plug, a cone, or a ball or any other object capable of holding a magnetic pin at its fastening portion.

A "flexible element" is an element made of any material that is compressible and/or extendable in a reversible manner. Such material can be intrinsically flexible like e.g. silicone rubber or polysulfide rubber or any other type of rubber, a polyurethane compound, latex, but it can also be flexible due to its geometrical construction or shape, like e.g. a spring made of metal. A ball joint made of rigid material such as metal is also to be considered a flexible element in the context of the present invention, since it allows for individual displacement of the magnetic pins at their separation portion.

In a preferred embodiment, said one or more flexible elements are an outer layer made of flexible material, wherein said outer layer covers a rigid core. More preferably, said outer layer comprises one or more O-rings as flexible elements. Most preferably, said outer layer consists of one or more O-rings as flexible elements. In a preferred embodiment, said holder is a plug. Said O-rings are preferably made of rubber.

In another preferred embodiment, the magnetic pins are fastened to the support plate via a ball joint.

In a preferred embodiment of the invention, the magnetic pins of the magnetic separation plate are flexible.

The terms "flexible" or "flexible magnetic pins", respectively, mean that the pins comprise one or more "flexible elements" at one or more of its portions.

In a further embodiment, the magnetic pins comprise a core containing two or more rigid elements that are displaceable with respect to each other, said magnetic pins further comprising a covering made of flexible material and embedding said rigid elements. Preferred rigid elements are balls or rings. More preferably, said rigid elements are cylinder-shaped discs.

In a further aspect of the invention, said flexible elements are wires.

It must be understood that combinations of the features relating to the magnetic separation plate are possible. Thus, in a preferred embodiment of the invention, the magnetic separation plate comprises magnetic pins that are intrinsically flexible as well as flexibly fastened.

Furthermore, the pins contain magnetic material or magnetizable material.

As the magnetic separation plate according to the invention can be used in a system comprising other elements it interacts with, the following is also an aspect of the invention:

A magnetic separation system for use in methods employing magnetic particles, said system comprising
   a magnetic separation plate as described above
   a multiwell plate comprising wells for receiving fluids containing said magnetic particles, said multiwell plate further comprising recesses in positions corresponding to a predetermined geometrical arrangement of the magnetic pins of said magnetic separation plate,
wherein the separation portions of said magnetic pins are reversibly inserted into said recesses in a separation position.

A "magnetic separation system" means a device or combination of devices suitable for the separation of components in a mixture by means of magnetic forces.

A "multiwell plate" is a device for receiving liquid substances or mixtures in receptacles, the "wells". The latter are usually arranged in a defined geometrical pattern. The "multiwell plate" can e.g. have 6, 12, 24, 48, 96, 384, 480 or 1536 "wells", but is not restricted to these numbers. The plate can further be made of transparent material, allowing for the passage of light e.g. for detection purposes in a photometric assay. Typically, a "multiwell plate" is made of plastics. In a preferred embodiment, the plastic is polypropylene. A "multiwell plate" does not have any specific restrictions with regard to the shape, size or volume of its "wells". Thus, a "multiwell plate" can be e.g. a deep-well plate, a microwell plate etc.

"Magnetic particles" are a magnetic or magnetizable solid phases. These particles may be preadapted to bind specific materials such as biological materials. Preadaptation can for example be achieved chemically (e.g. adding functional groups like amino groups to the particle surface) or biologically (e.g. coating the particle surface with antibodies or specific nucleic acid binding motives). Further, the "magnetic particles" preferably comprise a silica surface such as glass, thus facilitating binding of e.g. nucleic acids in the presence of chaotropic agents.

As an example for the application of such particles, their use in immobilizing nucleic acids after precipitation by adding salt and ethanol is described e.g. in Alderton R. P. et al., S., Anal. Biochem. 201 (1992) 166-169 and WO 91/12079. In this procedure, the nucleic acids are agglutinated along with the magnetic particles. The agglutinate is separated from the original solvent by applying a magnetic field and performing a wash step. After one wash step, the nucleic acids are dissolved in a Tris buffer.

Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin.

Magnetizable particular adsorbents proved to be very efficient and suitable for automatic sample preparation. Ferrimagnetic and ferromagnetic as well as superparamagnetic pigments are used for this purpose. The most preferred MGPs and methods using magnetic glass particles are those described in WO 01/37291. Particularly useful is the method according to R. Boom et al. (J Clin Microbiol. 28 (1990), 495-503).

"Reversibly" means that a process can be reverted without damaging components of a system. In particular, in the magnetic separation system according to the invention, the magnetic pins are "reversibly" inserted into the recesses of the multiwell plate, which means that pins and the recesses can be separated from one another by applying essentially the same force required as for insertion of the pins.

The "separation position" is a position in which the separation portion of the magnetic pins is inserted into the recesses of the multiwell plate with all or a part of their separation portion such that a magnetic field caused by the pins acts upon the magnetic particles within the wells of the multiwell plate.

The magnetic separation system according to the invention can advantageously be implemented into a larger analytical system. Thus, another aspect of the invention is an analytical system comprising the magnetic separation system according to the invention, said analytical system further comprising a pipetting module comprising a pipettor.

An "analytical system" is an arrangement of components such as instruments interacting with each other with the ultimate aim to analyze a given sample.

The "pipetting module" is one such component of an analytical system, wherein the pipettor, which may e.g. a robotic pipetting device, accomplishes aspirating and dispensing the sample, reagents or mixtures and thus transferring them between the other different components of said system.

For advantageous manipulation of the multiwell plate being part of the magnetic separation system, one aspect of the invention is the following:

An analytical system comprising the magnetic separation system as described above, said analytical system further comprising a multiwell plate handling module and/or a magnetic separation plate handling module.

A "multiwell plate handling module" is a device for moving the multiwell plate in spatial relation to the magnetic separation plate. It comprises a holder for the multiwell plate such as a drawer, and further a component like a robotic pivot arm to move said holder with or without the multiwell plate.

The "magnetic separation plate handling module" is a device for the handling of the magnetic separation plate according to the invention.

The handling modules set out above may also comprise DC-motors for movement of the plates and opening/closing/pressing a plate cover, sensors to identify the type of plate, or a barcode reader for identifying the sample.

In a preferred embodiment, the analytical system according to the invention further comprises one or more elements selected from the following group:

A reaction module containing the components of a chemical and/or biochemical reaction A detection module for detecting signals evoked by an analyte A storage module for reagents and/or disposables.

A "reaction module" can comprise a variety of vessels like tubes or plates, in which a reaction for the analysis of the sample such as Polymerase Chain Reaction or hybridization of antibodies takes place. The outer limits or walls of such vessels are chemically inert such that they do not interfere with the analytical reaction taking place within. Details of the Polymerase Chain Reaction are described infra.

A "detection module" can e.g. be an optical detection unit for detecting the result or the effect of the analysis procedure. An optical detection unit may comprise a light source, e.g. a xenon lamp, optics such as mirrors, lenses, optical filters, fiber optics for guiding and filtering the light, one or more reference channels, or a CCD camera.

A "storage module" module stores the necessary reagents to bring about a chemical or biological reaction important for analysis of the sample in question. It can also contain further components useful for the method of the invention, e.g. disposables such as pipet tips or vessels to be used as reaction receptacles within the reaction module.

Advantageously, the analytical system according to the invention further comprises a control unit for controlling system components.

Such a "control unit" may comprise a software for ensuring that the different components of said analytical system work and interact correctly and with the correct timing, e.g. moving components such as the pipettor to the multiwell plate in a coordinated manner. The control unit may also comprise a processor running a real-time operating system (RTOS), which is a multitasking operating system intended for real-time applications. In other words the system processor is capable of managing real-time constraints, i.e. operational deadlines from event to system response regardless of system load. It controls in real time that different units within the system operate and respond correctly according to given instructions.

A further aspect of the present invention is a method for the separation of magnetic particles, said method comprising the steps:

a) providing a multiwell plate containing magnetic particles and a biological sample in one or more wells, b) providing a magnetic separation plate comprising a support plate and magnetic pins in a predetermined geometrical arrangement, said magnetic pins having a fastening portion, an intermediate portion and a separation portion and being fastened to said support plate at their fastening portion, wherein said magnetic pins are individually displaceable at their separation portion, c) reversibly inserting said magnetic pins into recesses of said multiwell plate in positions corresponding to the predetermined geometrical arrangement of the magnetic pins of said magnetic separation plate for applying a magnetic field to said magnetic particles in said wells.

This method can be advantageously carried out with the magnetic separation plate and/or the magnetic separation system or analytical system according to the invention as described supra.

In a preferred embodiment, the method according to the invention further comprises the step of retracting the magnetic pins from the recesses of the multiwell plate for removing the magnetic field from the magnetic particles after step c).

Another aspect of the invention is the use of the magnetic separation plate according to the invention for the separation of magnetic particles.

If the material to be analyzed with the help of the plate, systems or method according to the invention is nucleic acids, there are various methods applicable in this context, one very significant method being the Polymerase Chain Reaction (PCR).

The "Polymerase Chain Reaction" (PCR) is disclosed, among other references, in U.S. Pat. Nos. 4,683,202, 4,683,195, 4,800,159, and 4,965,188. PCR typically employs two or more oligonucleotide primers that bind to a selected nucleic acid template (e.g. DNA or RNA). Primers useful for nucleic acid analysis include oligonucleotides capable of acting as a point of initiation of nucleic acid synthesis within the nucleic acid sequences of the microbial nucleic acid or quantitative standard nucleic acid. A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished. If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min). If the double-stranded template nucleic acid is denatured by heat, the reaction mixture is allowed to cool to a temperature that promotes annealing of each primer to its target sequence on the microbial nucleic acid and/or quantitative standard nucleic acid. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the nucleic acid to be analyzed. The temperature should be sufficient to synthesize an extension product from each primer that is annealed to a nucleic acid template, but should not be so high as to denature an extension product from its complementary template (e.g., the temperature for extension generally ranges from about 40° to 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min) The newly synthesized strands form a double-stranded molecule that can be used in the succeeding steps of the reaction. The steps of strand separation, annealing, and elongation can be repeated as often as needed to produce the desired quantity of amplification products corresponding to the microbial nucleic acid and/or quantitative standard nucleic acid. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Nucleic acid amplification reactions apart from PCR comprise the Ligase Chain Reaction (LCR; Wu D. Y. and Wallace R. B., Genomics 4 (1989) 560-69; and Barany F., Proc. Natl. Acad. Sci. USA 88 (1991)189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and QP-amplification (for a review see e.g. Whelen A. C. and Persing D. H., Annu. Rev. Microbiol. 50 (1996) 349-373; Abramson R. D. and Myers T. W., Curr Opin Biotechnol 4 (1993) 41-47).

Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as e.g. a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid. It is also possible to sequence the nucleic acid after further steps known to the expert in the field. A useful template-dependent nucleic acid polymerase is the ZO5 DNA polymerase and mutations thereof. Other template-dependent nucleic acid polymerases comprise e.g. Taq polymerase and Tth Polymerase.

FIGURE LEGENDS

FIG. 1: Perspective view of a magnetic separation plate.

FIG. 2: Bottom view of a multiwell plate.

FIG. 3: Schematic cross section of a multiwell plate and a magnetic separation plate interacting with each other.

FIG. 4: Schematic side view of an analytical system comprising a magnetic separation system.

Figure 1:
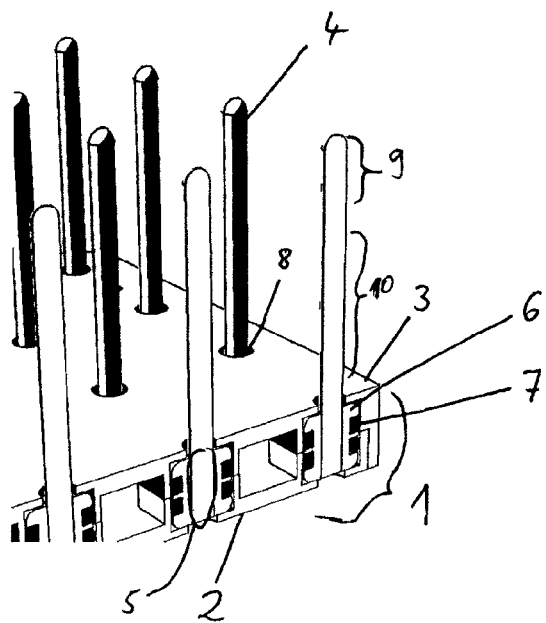
FIG. 1: Perspective view of a magnetic separation plate.

In this embodiment, the support plate (1) consists of a lower plate (2) and an upper plate (3) that are combined with each other. The magnetic pins (4) are fastened to the support plate at their fastening portion (5) via plugs (6) with the plate, the plugs each having two O-rings (7) made of flexible material. The pins protrude from the plate towards the outside via openings (8) in the upper part of the support plate. The O-rings confer flexibility to the magnetic pins relatively to the support plate such that their separation portions (9) are individually displaceable. The presence of two separate rings causes a reset force upon displacement of the pins' separation portion and therefore provides for a defined default position of the latter. The magnetic pins further possess an intermediate portion (10) between the fastening and the separation portion. The latter two portions are different in shape, thereby avoiding the risk of confusing the magnetic poles when assembling the magnetic separation plate. A potentially resulting alternating pole arrangement would inevitably lead to a weaker magnetic field, thus the preferred pattern of the poles is that all of them are arranged in the same orientation.

Figure 2:
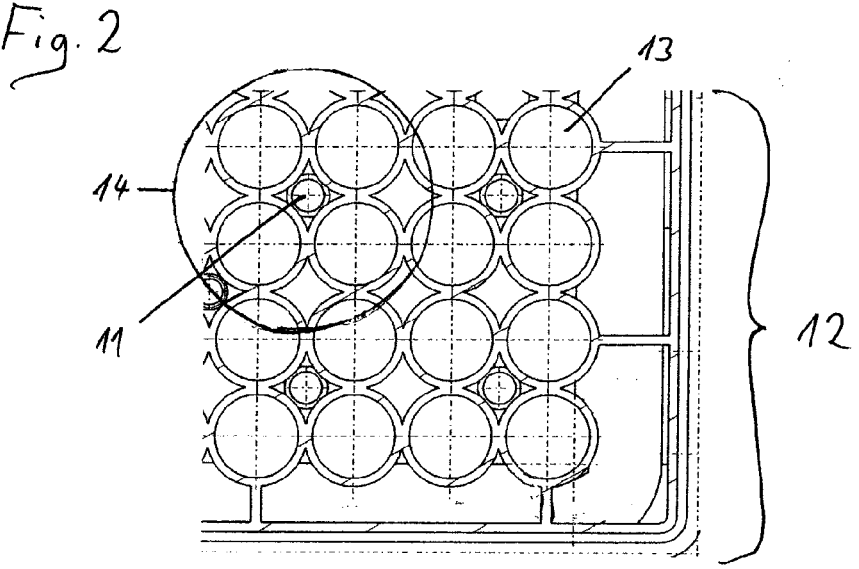

FIG. 2: Bottom view of a multiwell plate.

The magnetic pins of the magnetic separation plate (not shown) are inserted into preadapted recesses (11) within the multiwell plate (12). In this arrangement, every four wells (13, seen from below) are positioned around a recess for a magnetic pin causing a magnetic field (14) in the surrounding wells.

Figure 3:
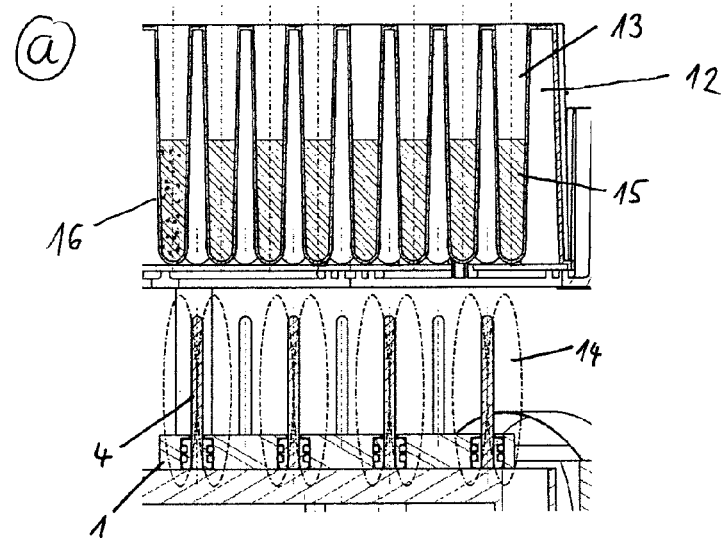
Figure 3:
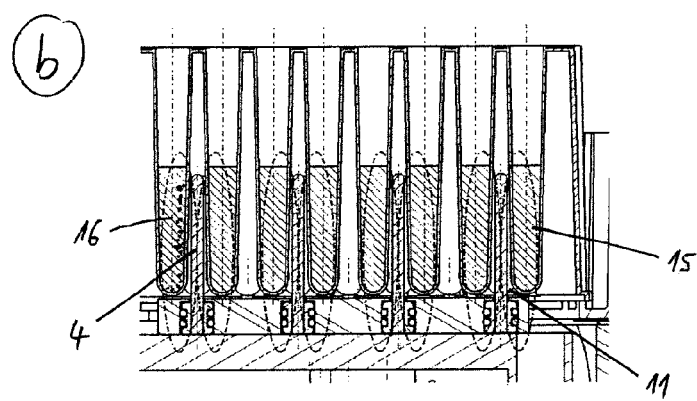
Figure 3:
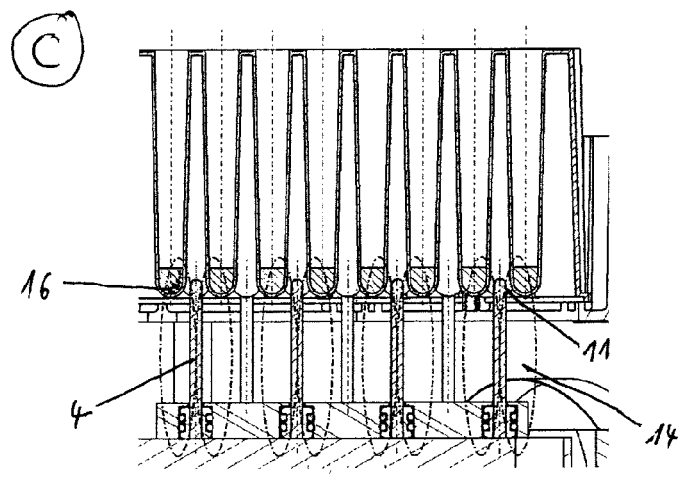

FIG. 3: Schematic cross section of a multiwell plate and a magnetic separation plate in three different positions interacting with each other.

In a first (inactive) position (FIG. 3a), the sample (15) within the wells (13) of the multiwell plate containing essentially homogeneously distributed magnetic particles (16) is not exposed to the magnetic field (14). The magnetic pins (4) are fastened to the support plate (1). The magnetic separation plate and the multiwell plate (12) are not in contact with each other.

In a second (separation) position (FIG. 3b), the magnetic pins (4) are inserted into the preadapted recesses (11) within the multiwell plate. The sample (15) is exposed to the magnetic field homogeneously throughout its entire height. The pins do not protrude higher than the fluid surface in order to avoid retraction of the magnetic particles (16) from the fluid. The magnetic particles are attracted to the walls of the wells.

In a third (separation) position (FIG. 3c), the magnetic pins (4) are inserted into the preadapted recesses (11) to a lesser extent, thus causing a stronger magnetic field (14) at the bottom of the wells than in the upper part. In this position, the magnetic particles (16) are attracted closer to the well bottom and are less prone to being accidentally retrieved from the well during removal of the supernatant.

Figure 4:
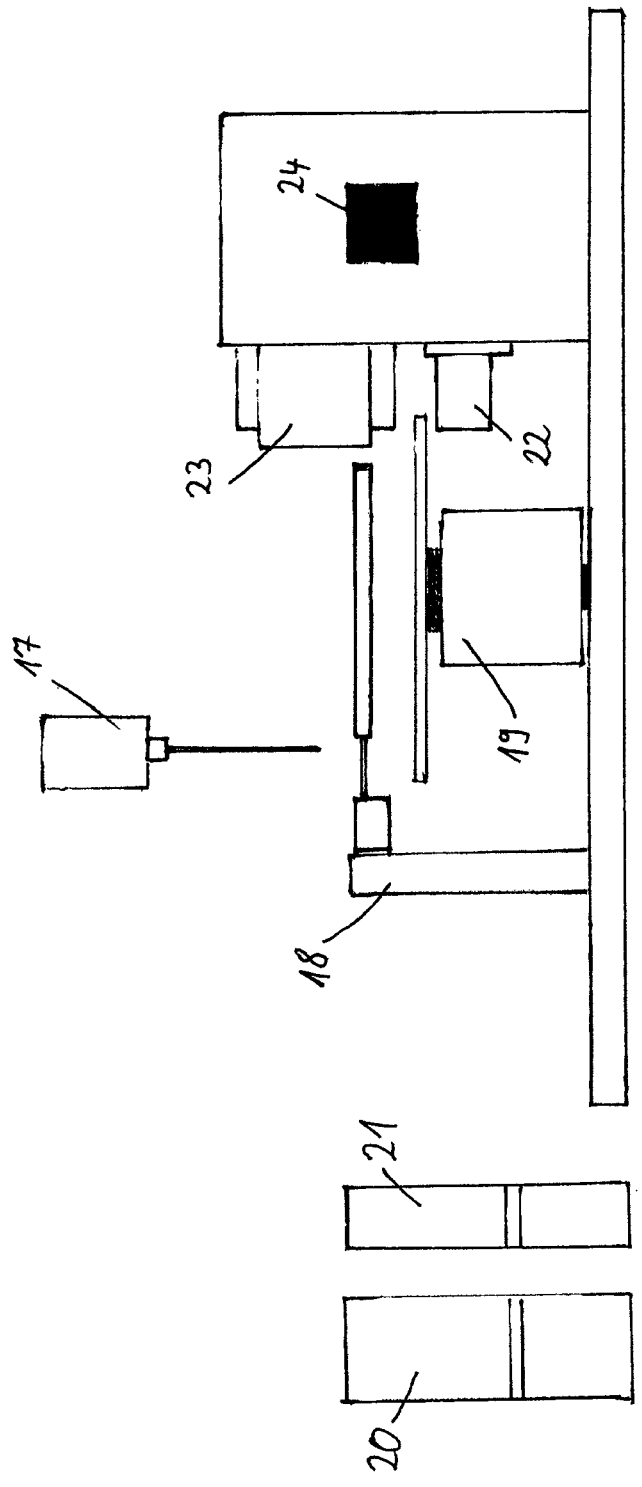

FIG. 4: Schematic side view of an analytical system comprising a magnetic separation system.

The analytical system comprises a moveable robotic pipettor (17) for aspirating and dispensing the sample, reagents or mixtures and thus transferring them between the other different components of said system. The system further comprises a multiwell plate handling module (18) for moving the multiwell plate in spatial relation to the magnetic separation plate, and a magnetic separation plate handling module (19) with an analogous function with respect to the magnetic separation plate. The multiwell plate (not depicted) is, in this embodiment, also the reaction module. The system also contains a storage to module for reagents (20) necessary to bring about a chemical or biological reaction important for the analysis of the sample in question, and further a storage module for disposables (21) such as pipette tips. Further present in this embodiment is an optical detection unit (22) with a light source (23). Also comprised by the system is a control unit (24) for controlling the other system components.

While the invention has been described in detail with reference to specific examples, it will be apparent to one skilled in the art that various modifications can be made within the scope of this invention. Thus the scope of the invention should not be limited by the examples described herein, but by the claims presented below.

I claim:

1. A magnetic separation system for use in methods employing magnetic particles, said system comprising
   a magnetic separation plate comprising a support plate and magnetic pins in a predetermined geometrical arrangement, said magnetic pins having a fastening portion, an intermediate portion and a separation portion and being fastened to said support plate at their fastening portion via a holder containing one or more flexible elements, wherein said magnetic pins are individually laterally displaceable at their separation portion;
   a multiwell plate comprising wells for receiving fluids containing said magnetic particles, said multiwell plate further comprising recesses in positions corresponding to the predetermined geometrical arrangement of the magnetic pins of said magnetic separation plate,
   wherein the separation portions of said magnetic pins are reversibly inserted into said recesses in a separation position.

2. An analytical system comprising the magnetic separation system of claim 1, said analytical system further comprising a pipetting module comprising a pipettor.

3. An analytical system comprising the magnetic separation system of claim 1, said analytical system further comprising a multiwell plate handling module and/or a magnetic separation plate handling module.

4. An analytical system comprising the magnetic separation system of claim 1, said analytical system further comprising one or more elements selected from the following group:
- A reaction module containing the components of a chemical and/or biochemical reaction
- A detection module for detecting signals evoked by an analyte
- A storage module for reagents and/or disposables.

5. The system of claim 4 further comprising a control unit for controlling the one or more elements.

6. The magnetic separation system of claim 1, wherein said pins are being fastened at their fastening portion via flexible elements comprising at least one element selected from plugs and one or more o-rings.

7. The magnetic separation system of claim 1, wherein said pins are being fastened at their fastening portion via flexible elements comprising a ball joint.

8. The magnetic separation system of claim 1, wherein said pins are flexible.

* * * * *